United States Patent [19]

Hodgkinson et al.

[11] Patent Number: 5,679,843
[45] Date of Patent: Oct. 21, 1997

[54] PROCESS FOR THE PRODUCTION OF N-PHOSPHONOMETHYLALYCINE AND SALTS THEREOF

[75] Inventors: Ian Hodgkinson; John Heathcote Atherton, both of Huddersfield, United Kingdom

[73] Assignee: Zeneca Limited, London, England

[21] Appl. No.: 556,319

[22] Filed: Nov. 13, 1995

[30] Foreign Application Priority Data

Nov. 11, 1995 [GB] United Kingdom ............... 9423254

[51] Int. Cl.⁶ ............................................. C07F 9/38
[52] U.S. Cl. ................................................. 562/17
[58] Field of Search .................................... 562/17

[56] References Cited

U.S. PATENT DOCUMENTS

| | | |
|---|---|---|
| 4,221,583 | 9/1980 | Gaertner et al. ............ 71/86 |
| 5,324,855 | 6/1994 | Morikawa et al. .......... 562/16 |
| 5,453,537 | 9/1995 | Morikawa et al. .......... 562/17 |

FOREIGN PATENT DOCUMENTS

| | | |
|---|---|---|
| 481394 | 4/1992 | European Pat. Off. . |
| 537786 | 4/1993 | European Pat. Off. . |
| 156933 | 8/1989 | Poland . |
| 94/22881 | 10/1994 | WIPO . |

OTHER PUBLICATIONS

Chemical Abstract 106:120064c(1987).

Primary Examiner—Gary Geist
Assistant Examiner—Jean F. Vollano
Attorney, Agent, or Firm—Joel G. Ackerman

[57] ABSTRACT

A process whereby N-phosphonomethylglycine (glyphosate) or its salts is manufactured by:

1) forming N-phosphonomethylglycinonitrile by reacting aminomethylphosphonic acid, an alkali metal cyanide and formaldehyde in aqueous solution at a pH in the range from 10 to 13 (and preferably from 11 to 11.5) whilst adding mineral acid at a rate sufficient to maintain the pH within the desired range, and thereafter 2) hydrolysing the N-phosphonomethylglycinonitrile product of Stage (1) to form a salt of N-phosphonomethylglycine and optionally 3) neutralising the salt of N-phosphonomethylglycine to form N-phosphonomethylglycine

10 Claims, No Drawings

PROCESS FOR THE PRODUCTION OF N-PHOSPHONOMETHYLALYCINE AND SALTS THEREOF

This invention relates to a process for the manufacture of N-phosphonomethylglycine.

N-phosphonomethylglycine and its salts are well known herbicides. It is known to prepare N-phosphonomethylglycine in a wide variety of ways and several processes are known which use aminomethylphosphonic acid as starting material.

In U.S. Pat. No. 4,221,582 there is described a process in which aminomethylphosphonic acid is first treated with an alkali metal hydroxide to give the mono alkali metal salt, and the pH at this point is in the range of 8.0 to 10.0. Formaldehyde is then added to produce a pH in the range of 5.5 to 7.0. This is then followed by the addition of sodium or potassium cyanide which causes the pH to increase, but concurrent additions of hydrochloric acid serve to maintain said pH in a range of 7.5 to 9.5. In an Example, the yield of product is stated to be 65%.

In EP 0537786 there is disclosed a process in which aminomethylphosphonic acid and glycolonitrile are reacted in the presence of an alkali metal hydroxide at a temperature not exceeding 60° C. and the product is then hydrolysed by the addition of alkali metal hydroxide in an amount sufficient to neutralise the resulting carboxylic acid (Reaction Scheme 1 below). The process is said to produce N-phosphonomethylglycine in a high yield.

Glycolonitrile is a toxic and hazardous compound whose transport and storage is subject to restrictions on safety grounds. In particular, stringent precautions are required if it is desired to handle volumes of glycolonitrile in excess of a few kilograms. For this reason glycolonitrile has serious disadvantages as a starting material for use in commercial practice.

It is known to prepare glycolonitrile by the reaction of sodium cyanide and formaldehyde under acidic conditions (Reaction Scheme 2 below) and, in view of the problems associated with the handling of glycolonitrile, it would be possible to consider the prior formation and use of glycolonitrile in aqueous solution. The resulting aqueous solution would then be used (without isolation of glycolonitrile) as feed-stock to a reaction such as Scheme 1. Whilst this is believed to be a feasible approach, the use of sodium cyanide under acidic conditions inevitably produces a partial pressure of hydrogen cyanide with the result that expensive plant is required to contain hydrogen cyanide and cope with any potential mal-operation of the process.

We have now found that it is possible to obtain N-phosphonomethylglycine in excellent yield by reacting aminomethylphosphonic acid, sodium cyanide and formaldehyde in a one-pot process without the need to pre-form glycolonitrile and under alkaline conditions such that hydrogen cyanide containment plant is not required.

Thus according to the present invention there is provided a process for the manufacture of N-phosphonomethylglycine or its salts which comprises 1) forming N-phosphonomethylglycinonitrile by reacting aminomethylphosphonic acid, an alkali metal cyanide and formaldehyde in aqueous solution at a pH in the range from 10 to 13 whilst adding mineral acid at a rate sufficient to maintain the pH within the desired range, and thereafter 2) hydrolysing the N-phosphonomethylglycinonitrile product of Stage (1) to form a salt of N-phosphonomethylglycine and optionally 3) neutralising the salt of N-phosphonomethylglycine to form N-phosphonomethylglycine free acid.

Stages (1) and (2) and optionally (3) may advantageously take place sequentially in a single reaction vessel.

The hydrolysis stage (2) preferably takes place using an alkali metal hydroxide with the formation of the corresponding alkali metal salt of N-phosphonomethylglycine. Free N-phosphonomethylglycine acid may if desired be recovered by acidification in optional stage (3). The alkali metal hydroxide is preferably sodium or potassium hydroxide. Sodium hydroxide is especially preferred.

The alkali metal cyanide used in stage (1) is preferably sodium or potassium cyanide. Sodium cyanide is especially preferred.

The mineral acid used in stage (1) is conveniently hydrochloric acid or sulphuric acid. Hydrochloric acid is preferred.

It is possible to mix the total reactant quantities of aminomethylphosphonic acid, alkali metal cyanide and formaldehyde and then add mineral acid at the rate necessary to maintain the desired pH. In practice however the rate of reaction, and hence the change in pH, may prove to be too fast to achieve an effective match between the change of pH and the rate of addition of the acid. It is preferred therefore to control the effective rate of reaction by the progressive addition of one or more reactants. Thus the one or more reactants can be added progressively over a period of time to the reaction mixture in order to reduce the effective reaction rate such that the pH can be conveniently maintained constant at the desired value by the corresponding progressive addition of acid.

Thus according to a further aspect of the present invention there is provided a process wherein, in stage 1, N-phosphonomethylglycinonitrile is formed by reacting aminomethylphosphonic acid, an alkali metal cyanide and formaldehyde at a pH in the range from 10 to 13, at least one of the reactants being added progressively over a period of time to reduce the effective reaction rate whilst adding mineral acid at a rate sufficient to maintain the pH within the desired range.

It is preferred that the one or more reactants which is added progressively is formaldehyde, or the alkali metal cyanide or both formaldehyde and the alkali metal cyanide. Equally, it is possible for example either to add the alkali metal cyanide progressively to the reaction product of aminomethylphosphonic acid and formaldehyde or to add the reaction product of aminomethylphosphonic acid and formaldehyde progressively to the alkali metal cyanide.

Thus for example it is possible:

a) to add the alkali metal cyanide progressively to a mixture (reaction product) of aminomethylphosphonic acid and formaldehyde; or b) to add the formaldehyde progressively to a mixture of alkali metal cyanide and aminomethylphosphonic acid; or c) to add both the alkali metal cyanide and formaldehyde simultaneously to aminomethylphosphonic acid; or d) to add the reaction product of aminomethylphosphonic acid and formaldehyde progressively to the alkali metal cyanide. Any combination of the above, for example the addition of formaldehyde and a proportion of the alkali metal cyanide to the aminomethylphosphonic acid and the remainder of alkali metal cyanide, is also possible provided at least one of the reactants is added progressively. In general however it is more convenient to add only one reactant progressively, and options (a) (or its variant (d)) and (b) above are preferred.

It is especially preferred in Stage (1) to add aqueous formaldehyde progressively to an aqueous solution of aminomethylphosphonic acid and alkali metal cyanide (Option (b) above). We have found that addition of the formaldehyde progressively to the other reactants tends to reduce the possibility of over-alkylation of aminomethylphosphonic acid and the undesired formation of N-phosphonomethyliminodiacetonitrile as a by-product. In addition the reaction of formaldehyde with aminomethylphosphonic acid (see scheme 3) is mildly exothermic and in commercial practice it is desirable therefore to add the formaldehyde progressively to the aminomethylphosphonic acid to avoid excessive generation of heat. Option (b) therefore provides for a shorter overall cycle time since the alkali metal cyanide and the aminomethylphosphonic acid can be rapidly mixed (no heat of reaction) to form the reactant mixture to which-the formaldehyde is then progressively added. In Option (a), the formaldehyde must be added slowly to the aminomethylphosphonic acid to avoid excessive heat generation in the formation of the reaction mixture and the alkali metal cyanide is then added progressively in Stage 1.

Whilst the scope of the present invention is not to be taken as being restricted by any one particular hypothesis as to the mechanism of operation thereof, it is believed that the process of the present invention operates according to Reaction Scheme (3) which is illustrated using sodium cyanide as the alkali metal cyanide. Whilst the existence of intermediate (II) in Reaction Scheme (3) is not proven beyond doubt, the proposed mechanism illustrates that each molecule of aminomethylphosphonic acid reacts with one molecule of formaldehyde and one molecule of cyanide ion to release one alkali metal cation which in turn requires one mole of mineral acid to be neutralised and maintain the pH. The addition of mineral acid can thus be matched on an equimolar basis with the rate of addition of formaldehyde (and optionally alkali metal cyanide) to maintain the required pH. Alternatively the pH can be monitored and maintained at the required value by the addition of appropriate quantities of mineral acid.

It is also to be noted that at the operating pH of the reaction, the aminomethylphosphonic acid starting material will be present in the form of its di-(alkali metal) salt and sufficient alkali metal hydroxide should therefore be supplied to the aqueous solution of aminomethylphosphonic acid and the alkali metal cyanide before reaction commences to raise the pH to the required value. It is desirable to add the alkali metal hydroxide to the aminomethylphosphonic acid before the addition of sodium cyanide to limit any production of hydrogen cyanide. It is preferred to form the di-sodium salt of aminomethylphosphonic acid and to adjust the starting pH in Stage 1 using sodium hydroxide as the alkali metal hydroxide.

The proportions of aminomethylphosphonic acid (present as its di-(alkali metal) salt, alkali metal cyanide and formaldehyde used in step (1) (once the addition of all the reactants is complete) are preferably essentially 1:1:1 on a molar basis. A slight excess of any one reactant, for example a variation from the stoichiometric value of plus or minus about 5%, may be used without detriment but use of a significant excess aminomethylphosphonic acid is an unnecessary waste of starting material (unless a re-cycle is involved), whilst use of a significant excess formaldehyde may result in over-alkylation and the formation of undesired by-products. The use of a slight excess of formaldehyde may be desirable to make up any loss to atmosphere of formaldehyde from the reaction mixture. Similarly, the use of a slight excess of alkali metal cyanide may be desirable to make up for any slight loss of cyanide due to hydrolysis.

It is not essential that the aminomethylphosphonic acid in the form of its disodium salt be completely dissolved in the aqueous solution at the start of reaction and we have found that any solid aminomethylphosphonic acid disodium salt present at the start of the reaction progressively dissolves as the reaction proceeds.

It is possible to use excess aminomethylphosphonic acid (for example up to 2 moles of aminomethylphosphonic acid per mole of formaldehyde) in combination with a recycle of aminomethylphosphonic acid and this may provide the advantage of a still further reduction in the formation of undesirable N-phosphonomethyliminodiacetic acid as by-product.

A variety of possible re-cycle procedures will occur to those skilled in the art. Thus for example the following procedure may be used to recover and re-cycle excess aminomethylphosphonic acid present in a product stream containing the sodium salt of N-phosphonomethylglycine- 1. The alkaline product stream is acidified (for example to pH 1.3) to precipitate N-phosphonomethylglycine which is recovered by filtration.

2. The pH of the filtrate (containing the excess aminomethylphosphonic acid and a smaller proportion of the N-phosphonomethylglycine remaining in solution) is adjusted to pH 2.5 by the addition of alkali and ferric sulphate solution is added to precipitate a water-insoluble complex Of both aminomethylphosphonic acid and N-phosphonomethylglycine whilst the pH is maintained at 2.5 by the addition of further alkali. The highly insoluble iron complex is removed by filtration, leaving only traces of aminomethylphosphonic acid and N-phosphonomethylglycine in solution together with any undesired by-product.

3. The iron complex is slurried in water and treated with alkali to raise the pH to 11.7. The resultant ferric oxide hydrate is filtered off to leave the recovered aminomethylphosphonic acid and N-phosphonomethylglycine present as their alkali metal salts in solution ready for re-cycle to the reaction stream.

Good yields of product are obtained when the pH of Reaction Stage (1) is within the specified range of from 10 to 13. It has been found however that improved yields are obtained when the pH is from 10.5 to 12, and an especially preferred pH range is from 10.5 to 11.5, for example from 11 to 11.5.

The progressive addition of the reactant (for example the formaldehyde or the alkali metal cyanide) to the reaction mixture conveniently takes place so that the charging of the reactant is spread more or less evenly over the reaction time. The reaction time of stage (1) may vary widely depending on the plant conditions but reaction times are typically from 20 minutes to 4 hours, for example from 40 minutes to 2 hours. As noted above, the mineral acid may be co-added with the formaldehyde, preferably in separate addition streams, in equimolar proportions or the pH may monitored and acid added in sufficient quantities to maintain the pH constant.

The reaction of stage (1) may take place within the range from 10° C. to 65° C. and preferably within the range 20° to 35° C., for example from 20° to 30° C. The reaction may conveniently take place at ambient temperature. Reaction stage (1) is exothermic and the temperature may be allowed to rise slightly within the foregoing range if desired. Cooling or heating may be provided if necessary to maintain the reaction temperature within the desired range.

Reaction Scheme (1) shows that the hydrolysis stage (2) requires 1 mole of alkali metal hydroxide per mole of N-phosphonomethylglycinonitrile which is present in the form of its di-(alkali metal) salt (i.e. 1 mole of alkali metal hydroxide is required in addition to the 2 moles of alkali metal hydroxide required at the start of stage (1) to convert aminomethylphosphonic acid to its di-(alkali metal) salt). Excess alkali metal hydroxide may be used for hydrolysis if desired but no particular benefit is obtained and the use of an excess of alkali metal hydroxide for hydrolysis will result in the formation of additional inorganic alkali metal salt during subsequent isolation of the N-phosphonomethylglycine. The hydrolysis conveniently takes place at elevated temperature, for example at a temperature of from 60° C. to the boiling point of the reaction mixture. The hydrolysis conveniently takes place at reflux. Pressure hydrolysis may be used if desired.

The product of the hydrolysis is an aqueous solution of the alkali metal salt of N-phosphonomethylglycine. The solution may be used as such or the salt of N-phosphonomethylglycine may be isolated, or N-phosphonomethylglycine acid may be precipitated by neutralisation of the solution with mineral acid, such as sulphuric or hydrochloric acid, in optional stage (3). N-phosphonomethylglycine thus recovered may subsequently be converted into other salts thereof such as the isopropylamine or trimethylsulphonium salt of N-phosphonomethylglycine.

The process of the present invention may be operated as a batch, continuous or semi-continuous process. If operating on a continuous basis it may be desirable to use a slightly higher reaction temperature to ensure that the aminomethylphosphonic acid present as its disodium salt at the start of the reaction remains in solution.

The invention is illustrated by the following Examples in which all parts and percentages are by weight unless otherwise stated.

EXAMPLE 1

Aminomethylphosphonic acid, 5.243 g at 100%, was slurried in 34 mls of distilled water and sodium hydroxide, 15 g at 23.5%, was added to raise the pH to 11.0. Sodium cyanide, 2.444 g at 95%, was dissolved in the aminomethylphosphonic acid solution and the temperature adjusted to 20° C. Formaldehyde, 2.845 g at 50%, was diluted to 30 mls with water then added to the aminomethylphosphonic acid/cyanide mixture over about 40 minutes whilst maintaining the pH at 11.0 by co-addition of hydrochloric acid, 38.5 g of 1.0M.

After allowing the reaction mixture to stir for a further 50 minutes, additional sodium hydroxide, 8.0 g at 23%, was added and the mixture was refluxed for 3 hours.

Phosphorus nmr showed the cooled reaction mixture to contain only N-phosphonomethylglycine, aminomethylphosphonic acid and a small proportion of N-phosphonomethyliminodiacetic acid. Integration of peak areas indicated the yield of N-phosphonomethylglycine to be 82.5% theory.

EXAMPLE 2

An aqueous solution of aminomethylphosphonic acid disodium salt (38.5 g at 26.3%; 0.091 grm-mol) was mixed with a solution of sodium cyanide (4.7 g at 95%; 0.091 grm-mol) in 12.2 g of distilled water. The pH of this solution was 11.0. Formaldehyde (7.4 g at 37%; 0.091 grm-mol) was diluted to 14% w/w with distilled water and then added to the solution of aminomethylphosphonic acid and sodium cyanide over 40 minutes at 20° to 25° C. The pH of the reaction mixture was kept at pH 11 by the addition of hydrochloric acid as required (approximately 8 g at 36%). After stirring for a further 50 minutes, sodium hydroxide (7.8 g at 47%; 0.091 grm-mol) was added and the preparation held at reflux for 40 minutes. On cooling the reaction mixture was analysed by $^{31}$Pnmr. The yield of N-phosphonomethylglycine was determined to be 92.4% of theory based on aminomethylphosphonic acid charged (6.1% aminomethylphosphonic acid was unreacted and 1.5% N-phosphonomethyliminodiacetic acid had been formed).

EXAMPLE 3

The procedure of Example 2 was repeated except that reaction temperature was maintained at 30°–35° C. The yield of N-phosphonomethylglycine was 90.4% based on aminomethylphosphonic acid charged.

EXAMPLE 4

Sodium hydroxide (10.5 g at 47%) was added to a slurry of aminomethylphosphonic acid (7.63 g) in distilled water (30 g) to raise the pH to 11.0. The solution was cooled to 20° to 25° C. using an external water-bath before adding formaldehyde (2.1 g at 37.4%) diluted with water (9 g) over approximately 40 minutes. At this stage phosphorous NMR and proton NMR showed that the aminomethylphosphonic acid had been converted into a new phosphorous species. The clear solution produced was added to a solution of sodium cyanide (3.54 g at 95%) dissolved in water (9 g) over a period of about 50 minutes whilst maintaining the temperature at 20° to 25° C. and the pH at 10 to 10.5 by the addition of hydrochloric acid. After stirring for approximately 30 minutes, sodium hydroxide (5.87 g at 47%) was added and the reaction mixture was heated to reflux for 3 hours to ensure complete hydrolysis of the N-phosphonomethylglycinonitrile. On cooling, the reaction mass was analysed by phosphorous NMR which showed the yield of N-phosphonomethylglycine to be 94.8% of theory.

EXAMPLE 5

Aminomethylphosphonic acid (7.63 g) was slurried in 30 ml water and the pH was adjusted to 11.0 with 47% caustic soda solution. Sodium cyanide (3.37 g) was dissolved in 7.6 ml water and the aminomethylphosphonic acid and sodium cyanide solutions were mixed and cooled to 20° to 25° C. Formaldehyde (5.61 g at 37.4%), diluted with 9 ml of water was added dropwise to the reaction mixture over 40 minutes, maintaining the temperature at 20° to 25° C. and the pH at between 11.0 and 11.5 by the simultaneous addition of 36.5% hydrochloric acid.

The resultant clear solution was stirred at 20° to 25° C. and pH 11.0 to 11.5 for a further 50 minutes before adding 47% caustic soda (6.8 g), heating to reflux and holding at this temperature for 3 hours. Subsequent analysis of the reaction mixture indicated that N-phosphonomethylglycine had been produced at a yield equivalent to 90.4% of theory.

EXAMPLE 6

The procedure of Example 5 was repeated using identical conditions but the reaction mixture was maintained at pH 12 to 12.5 in Stage 1. The yield was reduced to 80.3% of theory.

EXAMPLE 7

The procedure of Example 5 was repeated using identical conditions but the reaction mixture was maintained at pH 10.5 to 11 in Stage 1. The yield was 90.5% of theory.

EXAMPLE 8

The procedure of Example 5 was repeated using identical conditions but the reaction mixture was maintained at pH 10 to 10.5 in Stage 1. The yield was reduced to 89.5% of theory.

EXAMPLE 9

The procedure of Example 5 was repeated using identical conditions (and a pH in Stage 1 of 11.0 to 11.5) but the reaction mixture was maintained at a temperature of 35° to 40° C. in Stage 1. The yield was reduced to 85% of theory.

EXAMPLE 10

The procedure of Example 9 was repeated using identical conditions but the reaction of Stage 1 was started at a temperature of 45° to 50° C. and the temperature was then progressively reduced to 20° to 25° C. as the reaction proceeded. The yield was 88.5% of theory.

EXAMPLE 11

Cycle 1

Aminomethylphosphonic Acid (7.63 g, 0.07 grm-mol) was slurried in 30 g of water and the pH raised to 11 with 47% caustic soda solution. Sodium Cyanide (3.09 g at 100%, 0.063 grm-mol) was dissolved in 7.6 g of water and mixed with the aminomethylphosphonic acid solution before readjusting the pH to 11.0 with more alkali. Formaldehyde solution (5.01 g at 37.4%, 0.063 grm-mol) was diluted with 9 g of water and added to the reaction mixture over 40 minutes, maintaining the temperature at 20° to 25° C. and pH at 11 to 11.5 by the progressive addition of 36.5% hydrochloric acid.

The clear solution was stirred for 50 minutes before adding 47% caustic soda solution (6.0 g) and refluxing for 3 hours to complete the hydrolysis (Stage 2).

On cooling, Phosphorus nmr showed the reaction mass to consist of approximately 83 parts of N-phosphonomethylglycine, 15 parts of unreacted aminomethylphosphonic acid and 2 parts of N-phosphonomethyliminodiacetic acid on a molar basis.

An alkaline solution corresponding to that prepared above was analysed to contain 10.9% N-phosphonomethylglycine and 1.07% aminomethylphosphonic acid, as free acids, and a trace of N-phosphonomethyliminodiacetic acid. A 2.386 kg sample of this solution was acidified to pH 1.3 by the slow addition of hydrochloric acid (0.492 kg at 37.5%) and the N-phosphonomethyglycine acid precipitated on stirring at room temperature.

The precipitate was removed by filtration to leave a solution containing 1.0% w/w N-phosphonomethylglycine and 0.95% w/w aminomethylphosphonic acid. (i.e. 91% recovery of N-phosphonomethylglycine with no precipitation of aminomethylphosphonic acid).

The filtrates from above (502.9 g) were adjusted to pH 2.5 by the addition of caustic soda solution (2.7 g at 47%). Ferric sulphate solution (35.5 g at 45%) was slowly added whilst maintaining the pH at 2.5 by the further addition of caustic soda solution (10.4 g at 47%). The resultant mixture of water-insoluble N-phosphonomethylglycine and aminomethylphosphonic acid iron complex salts was removed by filtration.

Analysis of the filtrates showed them to contain less than 100 ppm of N-phosphonomethylglycine and less than 100 ppm of aminomethylphosphonic acid.

The mixed precipitate from above (75 g) was slurried with water and caustic soda solution (16.2 g at 47%) was slowly added to raise the pH to 11.7 and stirring was continued for a further 60 minutes. Insoluble ferric oxide hydrate was removed by double filtration to leave a colourless solution containing 4.9% w/w N-phosphonomethylglycine and 4.8% w/w aminomethylphosphonic acid (calculated as free acids). This corresponded to a 90% recovery of these components from their iron complexes allowing for the liquors in the ferric oxide which was retained for re-use.

Cycle 2

Fresh aminomethylphosphonic acid (5.75 g) at 100% was added to a 40.7 g portion of the filtrates from above to give a total of 0.07 grm-mol. A Stage 1 reaction between the aminomethylphosphonic acid, formaldehyde and sodium cyanide was then carried out using similar conditions to those described in "Cycle 1" above. In this case recycled PMG was present.

Analysis of the reaction mass showed that the yield of N-phosphonomethylglycine was 83%, the only other phosphorus species present being unreacted aminomethylphosphonic acid and a small amount of N-phosphonomethyliminodiacetic acid by-product.

COMPARISON 1

The procedure of Example 2 was repeated without the addition of hydrochloric acid. The starting pH of the solution of aminomethylphosphonic acid and alkali metal cyanide was pH 12 and rose progressively to pH 13.5.

The yield of N-phosphonomethylglycine in this case was only 58.4%, of theory based on aminomethylphosphonic acid charged. A greater quantity of N-phosphonomethyliminodiacetic acid was formed and a considerable amount of aminomethylphosphonic acid remained unreacted.

CHEMICAL FORMULAE
(in Description)

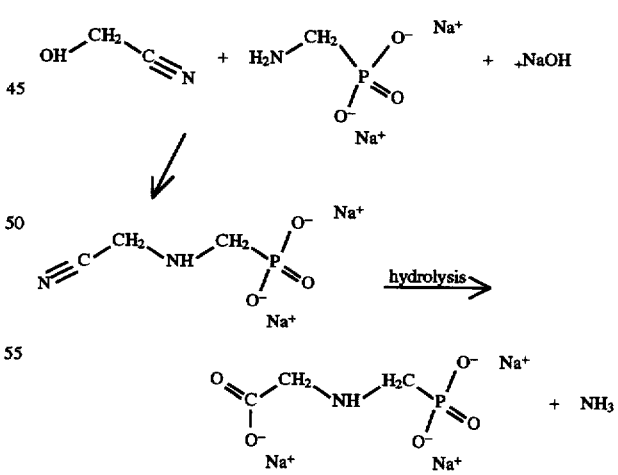

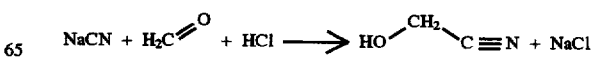

CHEMICAL FORMULAE
(in Description)
Scheme 3

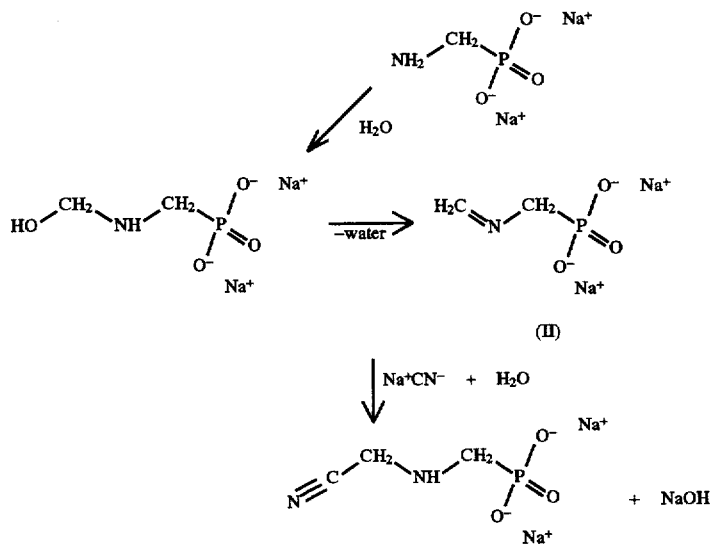

We claim:

1. A process for the manufacture of N-phosphonomethylglycine or its salts which comprises 1) forming N-phosphonomethylglycinonitrile by reacting aminomethylphosphonic acid, an alkali metal cyanide and formaldehyde at a pH in the range of 10 to 13, the formaldehyde being added progressively to an aqueous solution of aminomethylphosphonic acid and alkali metal cyanide over a period of time to reduce the effective reaction rate whilst adding mineral acid at a rate sufficient to maintain the pH within the desired range, and thereafter 2) hydrolyzing the N-phosphonomethylglycinonitrile product of Stage (1) to form a salt of N-phosphonomethylglycine and optionally 3) neutralizing the salt of N-phosphonomethylglycine to form N-phosphonomethylglycine free acid.

2. A process according to claim 1 wherein the alkali metal cyanide is sodium or potassium cyanide.

3. A process according to claim 1 wherein the proportions of aminomethylphosphonic acid, alkali metal cyanide and formaldehyde are essentially 1 to 1 to 1 on a molar basis.

4. A process according to claim 1 wherein the pH during Stage 1 is maintained at a pH within the range from 10.5 to pH 12.

5. A process according to claim 4 wherein the pH is maintained at a pH within the range from 10.5 to 11.5.

6. A process according to claim 1 wherein the temperature of Stage 1 is from 10° C. to 65° C.

7. A process according to claim 1 wherein the temperature is from 20° C. to 35° C.

8. A process according to claim 1 wherein the mineral acid used in Stage 1 is hydrochloric acid.

9. A process according to claim 1 wherein an alkali metal hydroxide is used in the hydrolysis of Stage 2.

10. A process according to claim 1 wherein the hydrolysis of Stage 2 takes place at a temperature of from 60° C. to the boiling point of the reaction mixture.

* * * * *